(12) United States Patent
Wilkes et al.

(10) Patent No.: US 9,549,859 B2
(45) Date of Patent: *Jan. 24, 2017

(54) METHOD OF INCORPORATING LEG ELASTICS IN A PANT-LIKE DISPOSABLE ABSORBENT GARMENT, AND GARMENT MADE THEREBY

(71) Applicant: Kimberly-Clark Worldwide, Inc., Neenah, WI (US)

(72) Inventors: Todd W. Wilkes, Appleton, WI (US); Lacey L. Poole, Appleton, WI (US); Joseph Andrew Mlinar, Appleton, WI (US); Marlene R. Dins, Appleton, WI (US); Russell Evan Thorson, Appleton, WI (US); Brian K. Rhodes, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 199 days.

This patent is subject to a terminal disclaimer.

(21) Appl. No.: 14/095,481

(22) Filed: Dec. 3, 2013

(65) Prior Publication Data

US 2014/0088542 A1    Mar. 27, 2014

Related U.S. Application Data

(62) Division of application No. 12/650,659, filed on Dec. 31, 2009, now Pat. No. 8,622,983.

(51) Int. Cl.
*A61F 13/15* (2006.01)
*A61F 13/49* (2006.01)
*A61F 13/496* (2006.01)

(52) U.S. Cl.
CPC ... *A61F 13/49017* (2013.01); *A61F 13/15609* (2013.01); *A61F 13/15747* (2013.01);
(Continued)

(58) Field of Classification Search
CPC ............. A61F 13/15699; A61F 13/49017; A61F 13/49019; A61F 13/4902; A61F 2013/49022
(Continued)

(56) References Cited

U.S. PATENT DOCUMENTS

| 4,770,656 A | 9/1988 | Proxmire et al. |
| 4,917,746 A | 4/1990 | Kons et al. |

(Continued)

FOREIGN PATENT DOCUMENTS

| WO | WO 96/04874 A1 | 2/1996 |
| WO | WO 2006/038837 A1 | 4/2006 |

(Continued)

*Primary Examiner* — Jacqueline Stephens
(74) *Attorney, Agent, or Firm* — Kimberly-Clark Worldwide, Inc.

(57) ABSTRACT

A pant-like garment having an elastomeric film laminate front panel and back panel. A front leg elastic member disposed adjacent the front panel leg edge. A back leg elastic member disposed adjacent the back panel leg edge. The absorbent garment having a leg elastic covering panel which extends between and interconnects the front panel to the back panel such that the front leg elastic member is sandwiched between the leg elastic covering panel and the front panel and such that the back leg elastic member is sandwiched between the leg elastic covering panel and the back panel. The length of the leg elastic covering panel is less than the garment length. An absorbent composite is attached to the leg elastic covering panel and a pair of side seams connects the front region to the back region to define a waist opening and a pair of leg openings.

8 Claims, 6 Drawing Sheets

(52) U.S. Cl.
CPC .. *A61F 13/15756* (2013.01); *A61F 13/15804* (2013.01); *A61F 13/496* (2013.01); *A61F 13/15699* (2013.01); *A61F 13/4902* (2013.01); *A61F 13/49019* (2013.01); *A61F 2013/49022* (2013.01); *Y10T 156/108* (2015.01); *Y10T 156/1049* (2015.01); *Y10T 156/1062* (2015.01)

(58) Field of Classification Search
USPC .................. 604/385.24, 385.25, 385.27, 385.29, 604/385.3
See application file for complete search history.

(56) References Cited

U.S. PATENT DOCUMENTS

| | | | |
|---|---|---|---|
| 5,275,676 | A | 1/1994 | Rooyakkers et al. |
| 5,643,396 | A | 7/1997 | Rajala et al. |
| 5,660,657 | A | 8/1997 | Rajala et al. |
| 5,745,922 | A | 5/1998 | Rajala et al. |
| 5,940,887 | A | 8/1999 | Rajala et al. |
| 6,049,916 | A | 4/2000 | Rajala et al. |
| 6,098,203 | A | 8/2000 | Rajala et al. |
| 6,217,690 | B1 | 4/2001 | Rajala et al. |
| RE37,154 | E | 5/2001 | Nomura et al. |
| 6,260,211 | B1 | 7/2001 | Rajala et al. |
| 6,284,081 | B1 | 9/2001 | Vogt et al. |
| 6,287,409 | B1 | 9/2001 | Stephany |
| 6,375,769 | B1 | 4/2002 | Quereshi et al. |
| 6,440,246 | B1 | 8/2002 | Vogt et al. |
| 6,533,879 | B2 | 3/2003 | Quereshi et al. |
| 6,540,857 | B1 | 4/2003 | Coenen et al. |
| 6,569,275 | B1 | 5/2003 | Popp et al. |
| 6,585,841 | B1 | 7/2003 | Popp et al. |
| 6,613,033 | B1 | 9/2003 | Popp et al. |
| 6,616,647 | B1 | 9/2003 | Krueger |
| 6,635,041 | B1 | 10/2003 | Popp et al. |
| 6,689,115 | B1 | 2/2004 | Popp et al. |
| 6,808,582 | B2 | 10/2004 | Popp et al. |
| 6,827,804 | B2 | 12/2004 | Otsubo et al. |
| 6,979,380 | B2 | 12/2005 | Thorson et al. |
| 7,000,260 | B2 | 2/2006 | Rajala et al. |
| 7,011,653 | B2 | 3/2006 | Imsangjan et al. |
| 7,045,031 | B2 | 5/2006 | Popp et al. |
| 7,172,669 | B2 | 2/2007 | Norrby |
| 7,179,343 | B2 | 2/2007 | Vaneperen et al. |
| 7,220,335 | B2 | 5/2007 | Van Gompel et al. |
| 7,326,311 | B2 | 2/2008 | Krueger et al. |
| 7,449,015 | B2 | 11/2008 | Otsubo et al. |
| 7,837,665 | B2 | 11/2010 | Van Gompel et al. |
| 2002/0193775 | A1 | 12/2002 | Shimoe |
| 2003/0051803 | A1 | 3/2003 | Sanders |
| 2003/0226634 | A1 | 12/2003 | Gardner |
| 2004/0122404 | A1 | 6/2004 | Meyer et al. |
| 2004/0210205 | A1 | 10/2004 | VanGompel et al. |
| 2005/0010188 | A1 | 1/2005 | Glaug et al. |
| 2005/0241747 | A1 | 11/2005 | Allen |
| 2006/0059598 | A1 | 3/2006 | Lohoff |
| 2006/0254708 | A1 | 11/2006 | Wada et al. |
| 2007/0293833 | A1 | 12/2007 | Wennerback |
| 2010/0298799 | A1 | 11/2010 | Wheeler |

FOREIGN PATENT DOCUMENTS

| | | |
|---|---|---|
| WO | WO 2006/093440 A1 | 9/2006 |
| WO | WO 2007/133127 A1 | 11/2007 |
| WO | WO 2009/031592 A1 | 3/2009 |
| WO | WO 2009/064225 A1 | 5/2009 |
| WO | WO 2011/048513 A2 | 4/2011 |
| WO | WO 2011/080655 A2 | 7/2011 |
| WO | WO 2012/080851 A1 | 6/2012 |

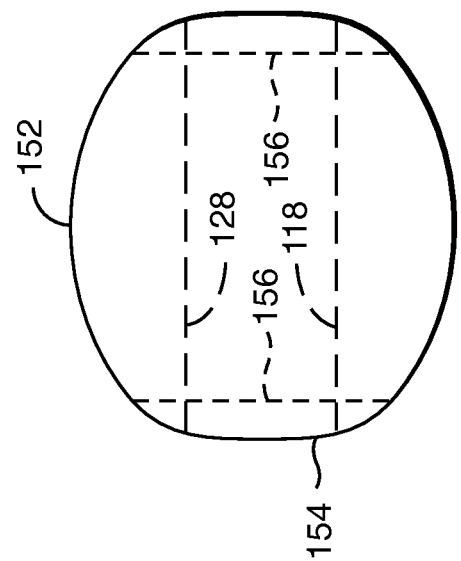
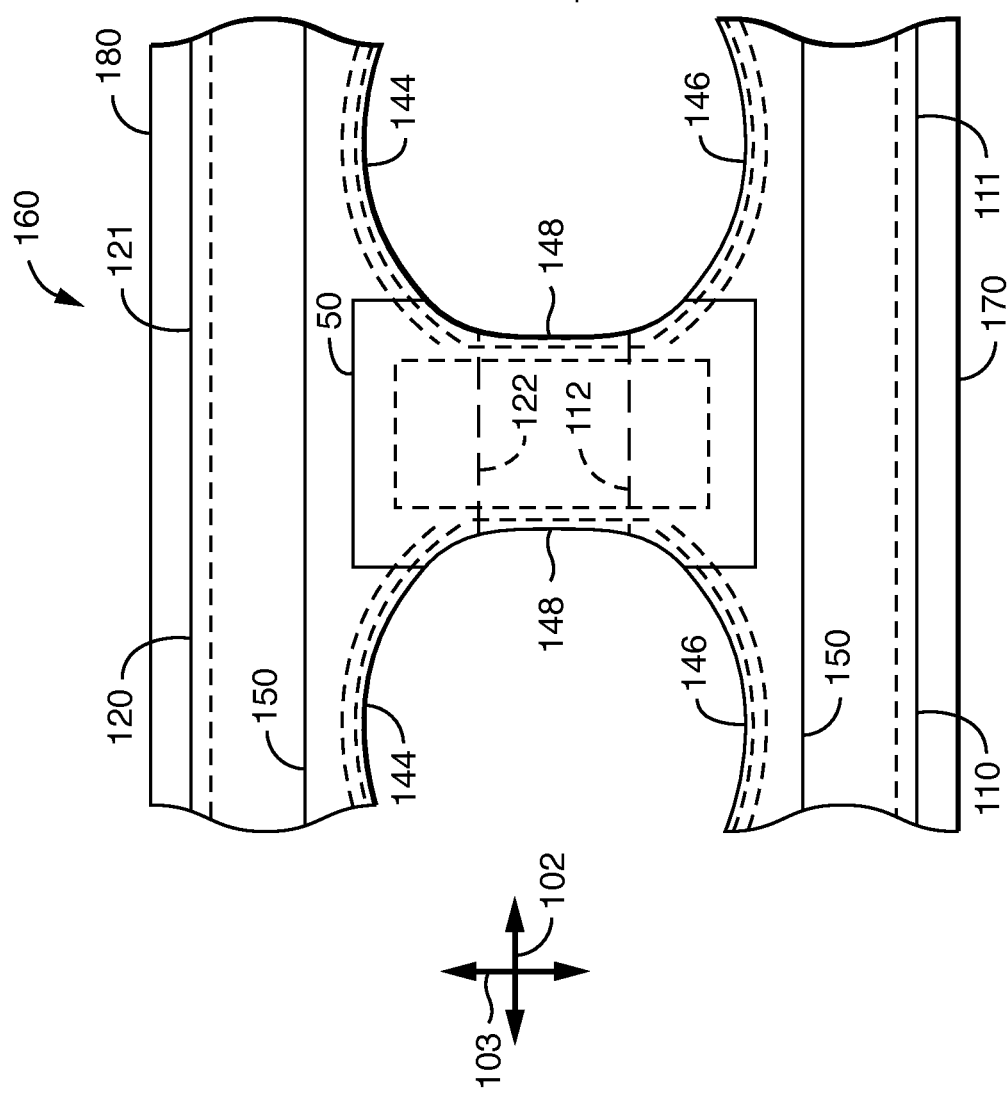

METHOD OF INCORPORATING LEG ELASTICS IN A PANT-LIKE DISPOSABLE ABSORBENT GARMENT, AND GARMENT MADE THEREBY

PRIORITY

This application is a divisional application of prior application Ser. No. 12/650,659 entitled Method of Incorporating Leg Elastics in a Pant-Like Disposable Absorbent Garment, and Garment Made Thereby and filed in the U.S. Patent and Trademark Office on Dec. 31, 2009. The entirety of the prior application is hereby incorporated by reference in this application.

BACKGROUND

People rely on disposable absorbent products in their everyday lives, including such articles as adult incontinence products, enuresis pants, training pants, and diapers. Many manufacturers seek to better meet the needs of users of such products. For example, there is a need to further improve fit, discretion, and leakage protection for many products. With certain products, such as adult incontinence underwear and enuresis pants, it is important that the garment feel as much as possible like "regular" underwear to promote an improved sense of normalcy to the wearer who suffers from incontinence or enuresis. Many conventional pant-like, pull-on style absorbent garments currently on the market employ a product chassis in which multiple threads of elastic are sandwiched between two nonwoven fabric layers. The strands extend around the body, such that the elastic forces extend primarily around the wearer's waist, as is the case with traditional cloth briefs. This design can provide good fit and leakage performance, but has the potential to be further improved in terms of looking and feeling even more like "regular" cloth underwear. In many instances, it is possible to also sandwich leg elastic strands between the nonwoven fabric layers.

One class of materials that offers the potential to make absorbent garments more "underwear-like" is that of elastomeric film laminates. Elastomeric film laminates are typically elastomeric films sandwiched between two nonwoven fabric layers. The films provide elastic properties similar to elastic threads, but offer a smoother, more uniform appearance. Some products currently on the market employ such elastomeric laminates, and utilize a "three-piece" pant construction in which front and back body panels are each constructed of an elastomeric film laminate and are connected together via an absorbent insert that extends between them. Such designs, however, can in certain instances introduce a difficulty. It is frequently desirable to include additional elasticization around the leg openings. In certain configurations, it may not be possible to simply sandwich additional leg elastic threads between the two nonwoven layers, such as when the elastomeric film laminate is a "pre-laminated" sandwich of an elastomeric film layer between two nonwoven layers. Instead, the leg elastic threads must be affixed to an outer surface of the elastomeric film laminate. In such instances, it is usually necessary to provide an additional layer of material to seal around the elastic threads and any associated adhesive, thereby holding the elastic threads in place on the elastomeric film laminate. Various efforts have been made to achieve this end, but they have been unsatisfactory. What is needed is improved methods of securing leg elastics to elastomeric film laminate body panels in disposable absorbent garments, in part to help, in certain instances, to simplify and improve the high speed manufacture of such garments.

SUMMARY OF THE INVENTION

To meet the above-described unmet needs in the art, a new process for making pant-like disposable garments, and a garment made thereby, has been invented.

In one aspect, the present invention relates to a method to incorporate leg elastic members into pant-like disposable absorbent garments. In particular embodiments, the method includes supplying an elastomeric film laminate first body panel web and an elastomeric film laminate second body panel web, both webs traveling in a machine direction, the first body panel web being spaced from the second body panel web in a cross-machine direction, the elastomeric film laminate first body panel web and the elastomeric film laminate second body panel web each comprising an elastomeric film layer and at least one nonwoven layer. The method can further include supplying a continuous first leg elastic member and a continuous second leg elastic member, both leg elastic members traveling in the machine direction. The method can further include attaching the first leg elastic member to the first body panel web and attaching the second leg elastic member to the second body panel web. The method can further include supplying a continuous leg elastic covering web traveling in the machine direction. The method can further include attaching the leg elastic covering web to both the first body panel web and the second body panel web so as to sandwich the first leg elastic member between the first body panel web and the leg elastic covering web and so as to sandwich the second leg elastic member between the second body panel web and the leg elastic covering web, thereby creating a composite web.

In another aspect, the present invention relates to a method for manufacturing a plurality of pant-like disposable absorbent garments. In particular embodiments, the method includes supplying an elastomeric film laminate first body panel web traveling in a machine direction and defining a waist edge extending in the machine direction and a leg edge extending in the machine direction. The method can further include supplying an elastomeric film laminate second body panel web traveling in the machine direction and defining a waist edge extending in the machine direction and a leg edge extending in the machine direction, the elastomeric film laminate first body panel web and the elastomeric film laminate second body panel web each comprising an elastomeric film layer sandwiched between two nonwoven facing layers. The method can further include positioning the first and second body panel webs in a non-overlapping relationship such that their respective leg edges are spaced apart from each other in a cross-machine direction a first distance, and such that their respective waist edges are spaced apart from each other in the cross-machine direction a second distance. The method can further include supplying a continuous first leg elastic member and a continuous second leg elastic member, both leg elastic members traveling in the machine direction. The method can further include attaching the first leg elastic member to the first body panel web at least partially adjacent the leg edge of the first body panel web, and attaching the second continuous leg elastic member to the second body panel web at least partially adjacent the leg edge of the second body panel web. The method can further include supplying a continuous leg elastic covering web traveling in the machine direction and which defines a first edge, a second edge, and a width extending between the first edge and the second edge in the cross-machine direction, wherein the covering web width is greater than said first distance and less than said second distance. The method can further include superposing the leg elastic covering web over the first and second body panel webs. The method can further include attaching the leg elastic covering web to both the first body panel web and the second body panel web so as to sandwich the first leg elastic member between the first body panel web and the leg elastic covering web and so as to sandwich the second leg elastic member between the second body panel web and the leg elastic covering web. The method can further include attaching an absorbent composite to the leg elastic covering web to create a composite garment web. The method can further include folding the composite garment web along a centerline that extends in the machine direction, such that the first body panel web waist edge is brought into close proximity with the second body panel web waist edge; attaching the first body panel web to the second body panel web along a series of garment side seam bonds spaced apart in the machine direction; and cutting the composite garment web at a series of cut locations spaced apart in the machine direction to create the plurality of pant-like disposable absorbent garments.

In yet another aspect, the present invention relates to a pant-like disposable absorbent garment. In particular embodiments, the garment defines a longitudinal direction and a lateral direction perpendicular to the longitudinal direction. The garment has a front region defining a front waist end edge, a back region defining a back waist end edge, and a crotch region longitudinally between the front and back regions. The crotch region defines two laterally opposed crotch side edges, and the garment defines a garment length extending from the front waist end edge to the back waist end edge. The garment includes an elastomeric film laminate front panel which defines a front panel waist edge, a front panel leg edge spaced longitudinally inward from the front panel waist edge, and first and second laterally opposed front panel side edges which extend longitudinally between the front panel waist edge and the front panel leg edge. The garment further includes an elastomeric film laminate back panel which defines a back panel waist edge, a back panel leg edge spaced longitudinally inward from the back panel waist edge, and first and second laterally opposed back panel side edges which extend longitudinally between the back panel waist edge and the back panel leg edge. The front panel is longitudinally spaced apart from the back panel. The garment further includes at least one front leg elastic member disposed adjacent the front panel leg edge, and at least one back leg elastic member disposed adjacent the back panel leg edge. The garment further includes a leg elastic covering panel which extends between and interconnects the front panel to the back panel such that the front leg elastic member is sandwiched between the leg elastic covering panel and the front panel and such that the back leg elastic member is sandwiched between the leg elastic covering panel and the back panel. A length of the leg elastic covering panel is less than the garment length. The garment can further include an absorbent composite attached to the leg elastic covering panel, as well as a pair of side seams connecting the front region to the back region, thereby defining a waist opening and a pair of leg openings.

In particular embodiments, the present invention can provide an efficient and process friendly technique to cover and hold in place leg elastic members in a pant-style disposable garment that employs elastomeric film laminates, particularly "pre-made" or "pre-laminated" elastomeric film laminates.

BRIEF DESCRIPTION OF THE FIGURES

FIG. 1a representatively illustrates a cross-sectional view of the first body panel web of FIG. 1 taken along line 1a-1a.

FIG. 2a is a cross-sectional view of the process portion depicted in FIG. 2, as viewed along line 2a-2a.

FIG. 3 is a top view of a composite web of a process akin to that depicted in FIG. 1, viewed in the vicinity of the process indicated by the brackets numbered "3," but showing an alternative embodiment of the process.

FIG. 3a representatively illustrates a removed portion of the composite web depicted in FIG. 3.

DEFINITIONS

Figure 1:
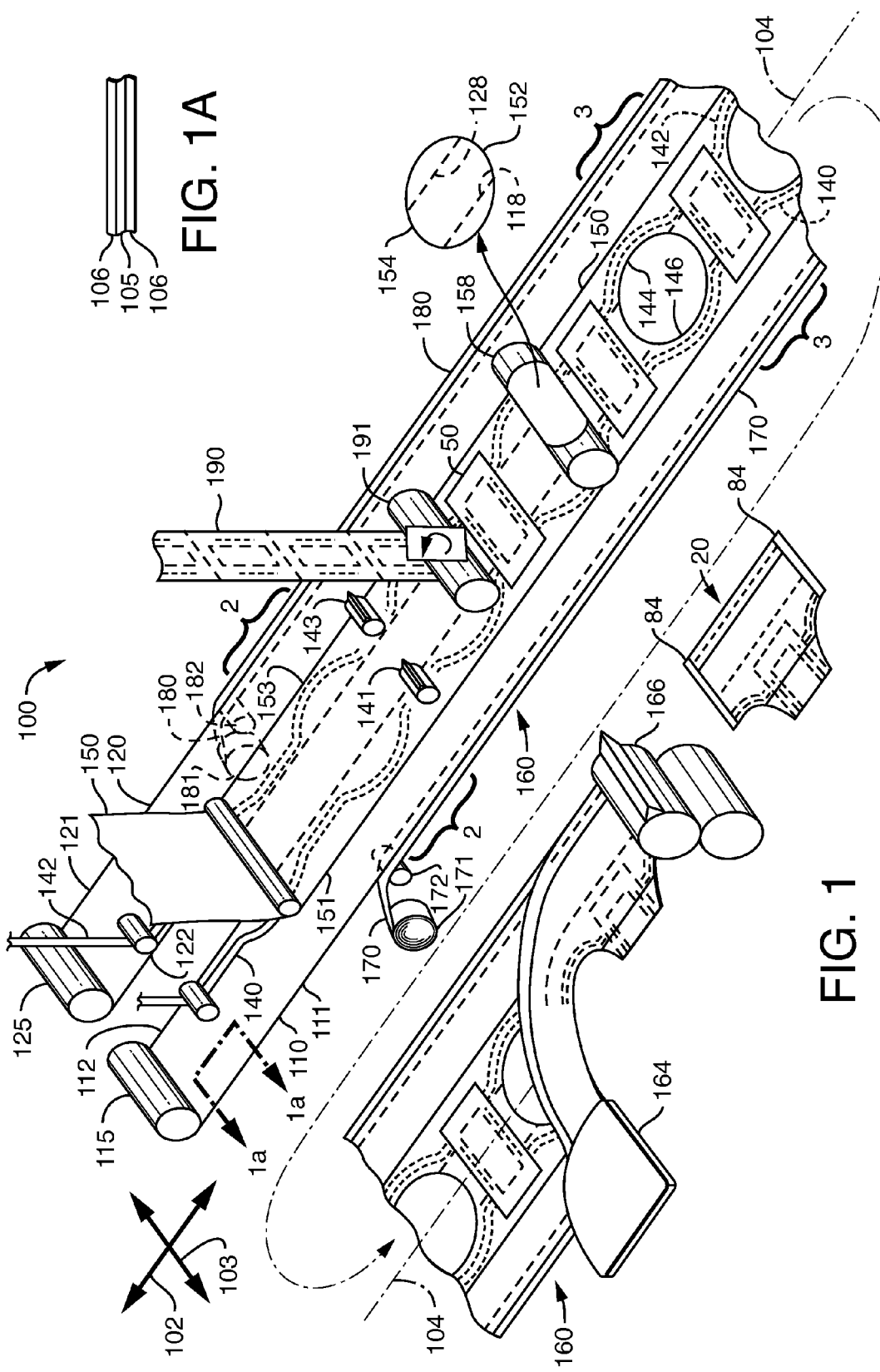
FIG. 1 representatively illustrates a perspective view of one embodiment of a manufacturing process incorporating principles of the process aspect of the present invention.

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

"Integral" is used to refer to various portions of a single unitary element rather than separate structures bonded to or placed with or placed near one another.

"Layer" when used in the singular can have the dual meaning of a single element or a plurality of elements.

"Member" when used in the singular can have the dual meaning of a single element or a plurality of elements.

These terms may be defined with additional language in the remaining portions of the specification.

DETAILED DESCRIPTION OF EXEMPLARY EMBODIMENTS

Reference to FIGS. 1-7 shall be made in describing various aspects and embodiments of the invention. It should be noted that the embodiments depicted in FIGS. 1-7 are merely representative examples of the process and garment aspects of the invention. Although for illustrative purposes certain features of the present invention shall be described and illustrated with respect to an adult incontinence garment, the various aspects and embodiments of the present invention are also suitable for use with disposable diapers, disposable swim pants, disposable training pants, disposable enuresis garments, and the like. Unless otherwise stated, all length and width dimensions referred to herein contemplate that such dimensions are measured while the garment or web is in a laid-flat and fully stretched condition, and prior to (in the case of garment dimensions) the joining of the front and back regions along side seams. Furthermore, unless otherwise stated, if a length or width measurement varies depending on where the measurement is taken (for example, if a scalloped edge causes a dimension to vary depending on where along the scalloped edge the measurement is taken), the length or width measurement for purposes herein is the maximum length or width that can be measured for that feature.

The present invention relates in certain aspects to techniques to incorporate leg elastic members into pant-like disposable absorbent garments, and to methods for manufacturing a plurality of pant-like disposable absorbent garments employing such techniques. In particular embodiments, as representatively illustrated in FIGS. 1 and 2, the method 100 includes supplying an elastomeric film laminate first body panel web 110 (such as via roll supply 115) and an elastomeric film laminate second body panel web 120 (such as via roll supply 125), both webs traveling in a machine direction 102. The first body panel web 110 is spaced from the second body panel web 120 in a cross-machine direction 103. The elastomeric film laminate first body panel web 110 and the elastomeric film laminate second body panel web 120 each comprise an elastomeric film layer 105 and at least one nonwoven layer 106. Preferably, the elastomeric film layer 105 is sandwiched between two nonwoven layers 106, 106. U.S. Patent Application Publications US 2008/0095978 and US 2009/0197041, both assigned to Kimberly-Clark Worldwide, Inc. and incorporated by reference herein to the extent not inconsistent herewith, provide examples of technology suitable for use in creating elastomeric film laminates suitable for use with the present invention, although other elastomeric film laminates can also be used.

In particular embodiments, the elastomeric film laminate first body panel web 110 defines a waist edge 111 that extends in the machine direction 102 and a leg edge 112 that extends in the machine direction 102. Similarly, the elastomeric film laminate second body panel web 120 in particular embodiments defines a waist edge 121 that extends in the machine direction 102 and a leg edge 122 that extends in the machine direction 102. The method further can comprise positioning the first and second body panel webs 110/120 in a non-overlapping relationship such that their respective leg edges 112/122 are spaced apart from each other in a cross-machine direction 103 a first distance 130, and such that their respective waist edges 111/121 are spaced apart from each other in the cross-machine direction 103 a second distance 132.

Figure 2:
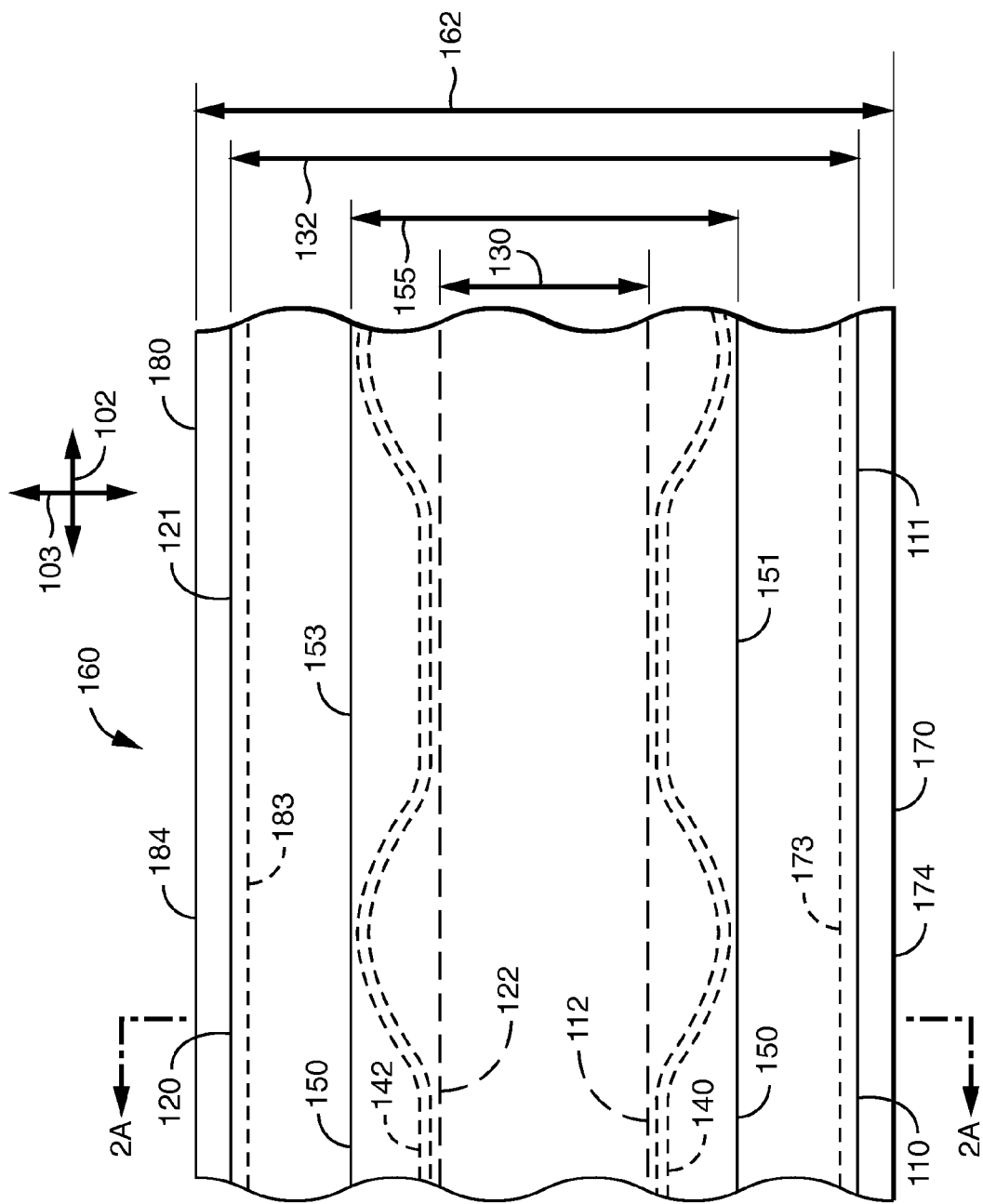
FIG. 2 is a top view of the composite web of the process embodiment depicted in FIG. 1, viewed in the vicinity of the process indicated by the brackets numbered "2".
Figure 2A:
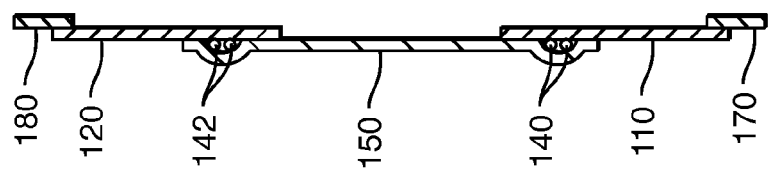
Figure 4:
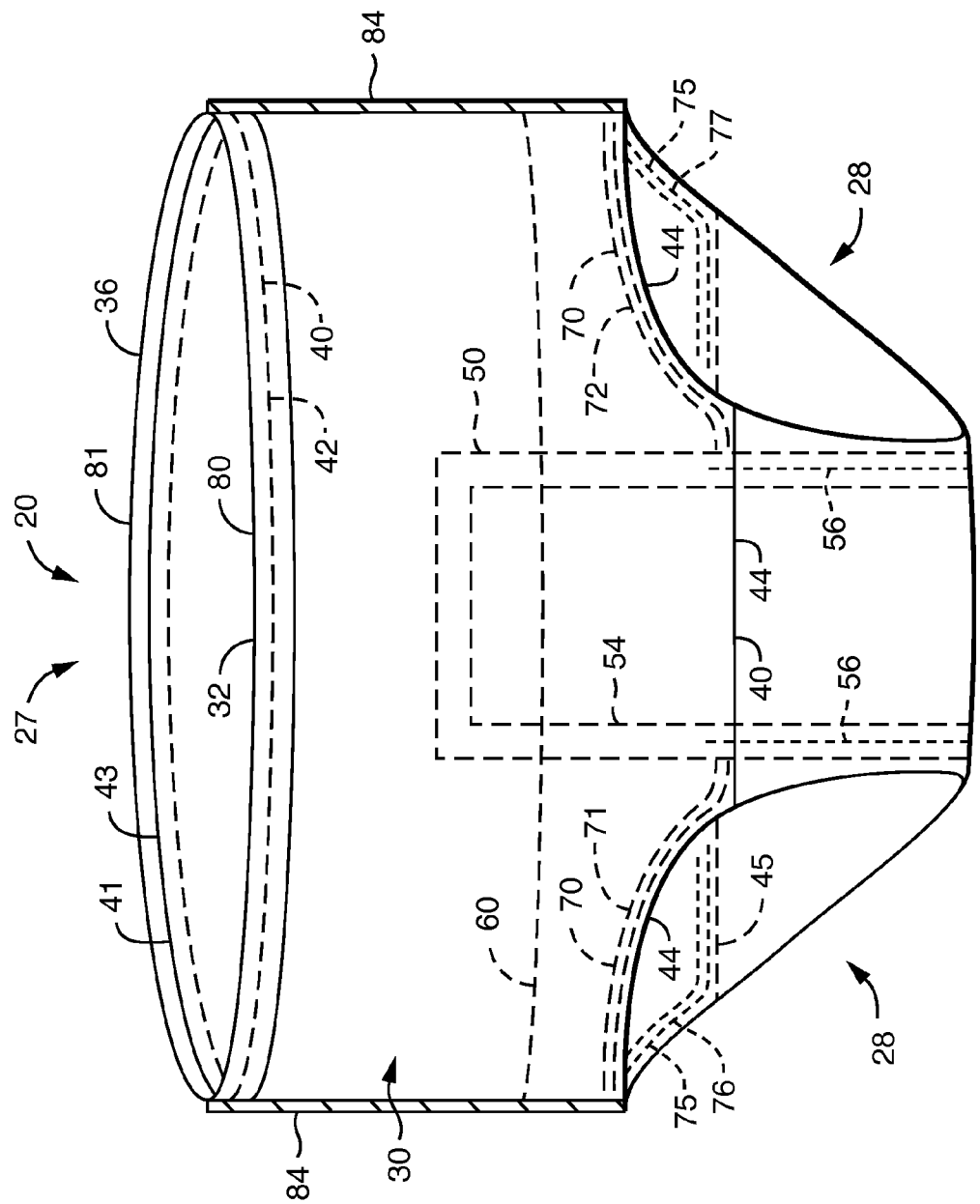
FIG. 4 representatively illustrates a front perspective view of a disposable absorbent article incorporating principles of the present invention.
Figure 5:
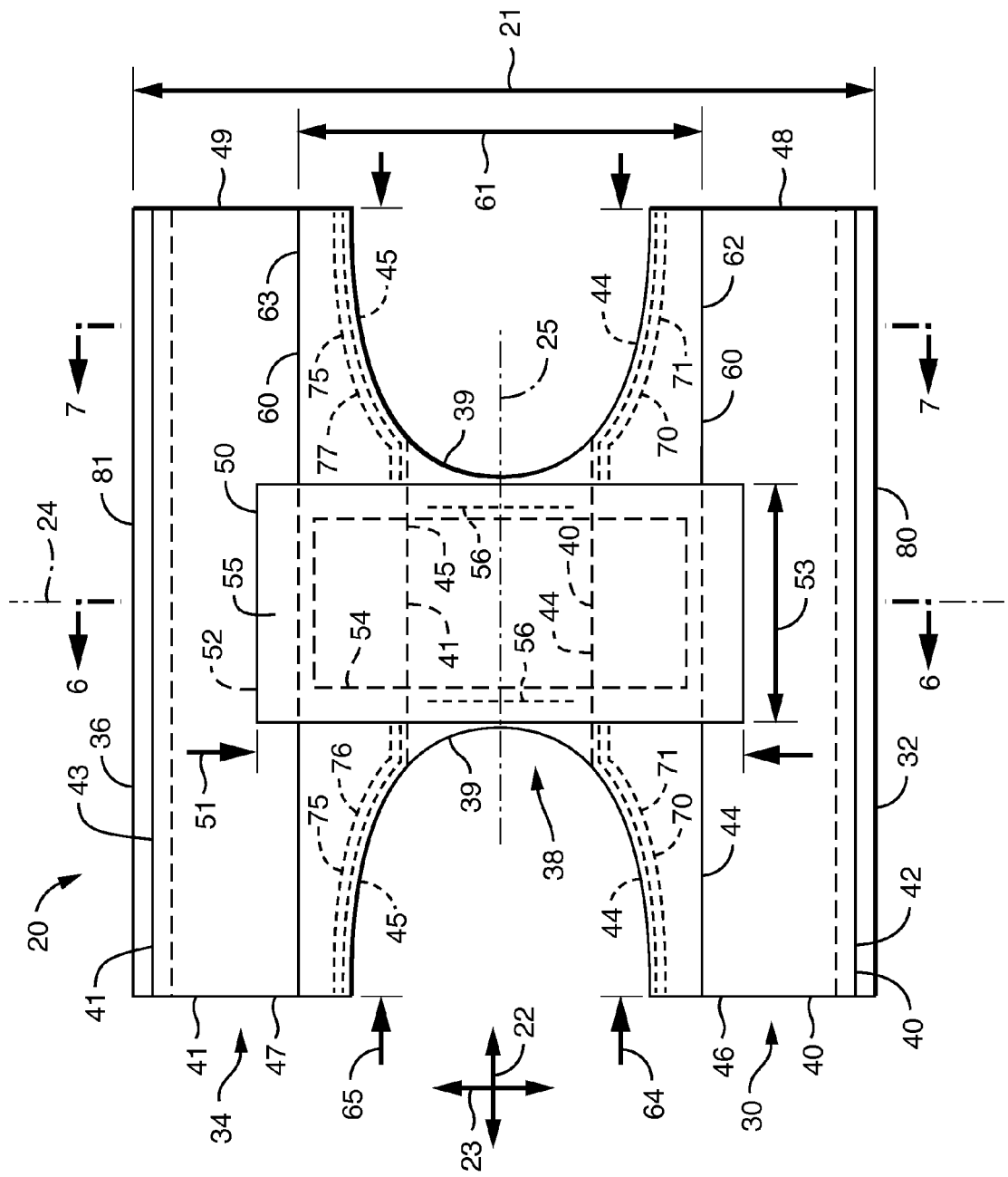
FIG. 5 representatively illustrates a plan view of a disposable absorbent article incorporating principles of the present invention, shown in a longitudinally and transversely stretched and laid-flat condition, prior to the joining of the front and back waist regions, and showing the surface of the article that faces toward the wearer when the article is worn.
Figures 6, 7:
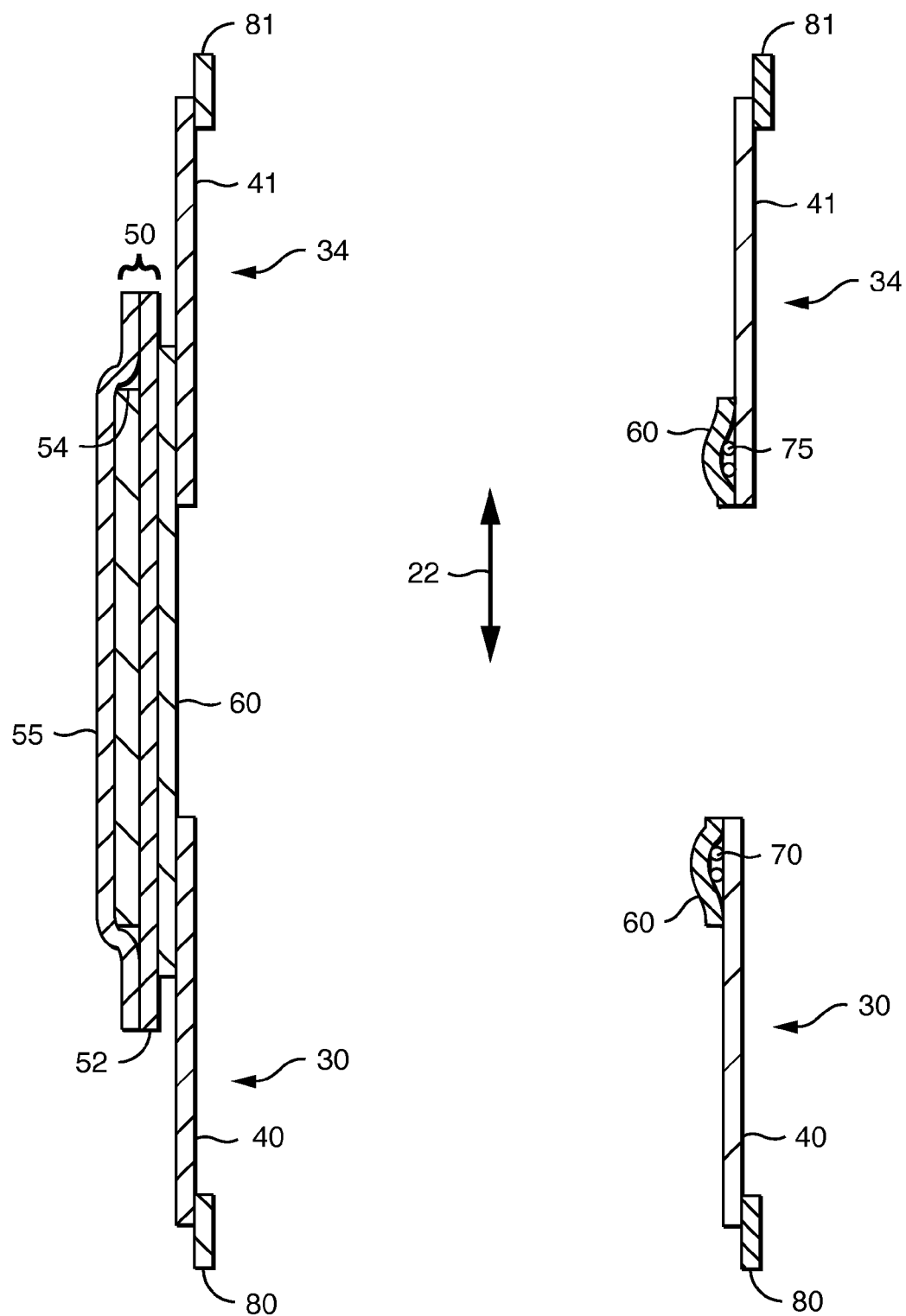
FIG. 6 is a cross-sectional view of the article of FIG. 5 as viewed along line 6-6.
FIG. 7 is a cross-sectional view of the article of FIG. 5 as viewed along line 7-7.

In particular embodiments, the method further includes supplying a continuous first leg elastic member 140 and a continuous second leg elastic member 142, both leg elastic members 140/142 traveling in the machine direction 102. Each leg elastic member 140/142 can comprise a single ribbon, strand, or thread (or the like) of elastic material, or each can comprise two (as shown in the example of FIGS. 1 and 2), three, or more ribbons, strands, or threads (or the like) of elastic material. The method further includes attaching the first leg elastic member 140 to the first body panel web 110 and attaching the second leg elastic member 142 to the second body panel web 120. Desirably, as representatively illustrated in FIGS. 1 and 2, the first leg elastic member 140 is attached to the first body panel web 110 at least partially adjacent the leg edge 112 of the first body panel web 110, and the second continuous leg elastic member 142 is attached to the second body panel web 120 at least partially adjacent the leg edge 122 of the second body panel 120. In certain embodiments, the first leg elastic member 140 extends in the machine direction 102 in a straight-line path, and the second leg elastic member 142 extends in a non-straight-line path in the machine direction 102. In other embodiments, such as that representatively illustrated in FIGS. 1 and 2, both the first leg elastic member 140 and the second leg elastic member 142 extend in a non-straight-line path in the machine direction 102. Elastic ribbons, strands, threads, and the like suitable for use in disposable absorbent garments are known in the art, one example being LYCRA brand elastic filaments, available from the Dupont Corporation. In certain embodiments, it may be desirable to reduce or eliminate the ability of the elastic strands to impart gathering forces in selected regions of an absorbent garment. For example, if it is desired to reduce or eliminate the gathering capacity of the elastic strands in the laterally central region of the garment (such as over the absorbent composite 50), the elastic strands may be severed, such as via front leg elastic chopper 141 and back leg elastic chopper 143, so that the elastic strands "snap back" a selected distance and such that the elastic strands do not pass over the laterally central region of the garment. Such configuration is depicted in FIGS. 1 and 3-6.

The method further comprises supplying a continuous leg elastic covering web 150 traveling in the machine direction 102. The leg elastic covering web 150 may comprise, for example, any suitable nonwoven material, such as spunbond, spunbond-meltblown laminates, bonded-carded webs, and the like. In particular embodiments, such as that representatively illustrated in FIGS. 1 and 2, the leg elastic covering web 150 defines a first edge 151, a second edge 153, and a width 155 extending between the first edge 151 and the second edge 153 in the cross-machine direction, and the covering web width 155 is greater than the first distance 130 and less than the second distance 132. After superposing the leg elastic covering web 150 over (or under) the first and second body panel webs 110/120, the method further comprises attaching the leg elastic covering web 150 to both the first body panel web 110 and the second body panel web 120 so as to sandwich the first leg elastic member 140 between the first body panel web 110 and the leg elastic covering web 150 and so as to sandwich the second leg elastic member 142 between the second body panel web 120 and the leg elastic covering web 150, thereby creating a composite web 160. The composite web defines a composite web width 162 which extends in the cross-machine direction 103, which is the width between the two transversely outermost edges of the composite process web assembly. In particular embodiments, the composite web width 162 is greater than the cross-machine direction width 155 of the leg elastic covering web 150.

In particular embodiments, the method can comprise supplying a first waistband web 170 (such as via roll supply 171) and a second waistband web 180 (such as via roll supply 181), and can further comprise attaching the first waistband web 170 to the first body panel 110 (such as at attachment station 172) and attaching the second waistband web 180 to the second body panel 120 (such as at attachment station 182). The waistband webs can be inherently elastomeric (such as via the use of an elastomeric film laminate material). Alternatively, waist elastic strands could be affixed to the front and/or back waistband webs to impart elasticity thereto. For example, the waistband webs could be inherently non-elastomeric but made to be elastomeric by affixing elastic strands thereto (such as by sandwiching elastic strands between two nonwoven webs or by enveloping elastic strands within a single, "C-folded" nonwoven web). Each first elastic waistband web defines a proximal edge 173 and a distal edge 174, and each second waistband web defines a proximal edge 183 and a distal edge 184. In embodiments that include waistband webs, the width 162 of the composite web 160 is the width extending in the cross-machine direction between the first waistband web distal edge 174 and the second waistband web distal edge 184, as is representatively illustrated depicted in FIG. 2.

The method can in particular embodiments further comprise removing portions 152 of the leg elastic covering web 150. In addition, the method can further comprise removing portions 128 of the second body panel web 120, removing portions 118 of the first body panel web 110, or removing both portions 128 of the second body panel web 120 and portions 118 of the first body panel web 110. Removal of portions 128 of the second body panel web 120 defines a series of back leg opening edges 144 spaced apart in the machine direction 102. Similarly, removal of portions 118 of the first body panel web 110 defines a series of front leg opening edges 146 spaced apart in the machine direction 102. It can be seen that in the example representatively illustrated in FIG. 1, the removed portion 154 of the composite web 160 includes a removed portion 152 of the covering web 150, a removed portion 118 of the first body panel web 110, and a removed portion 128 of the second body panel web 120. In addition or in the alternative to removal of portions 118/128 of the front and/or back body panel webs, particular embodiments of the method can include removing portions 156 of the absorbent composite 50 (discussed below) to define a series of crotch edges 148 spaced apart in the machine direction 102. Such an embodiment is representatively illustrated in FIG. 3. Note that in such an embodiment, the removed portion 154 of the composite web 160 (representatively illustrated in FIG. 3a) includes a removed portion 152 of the covering web 150, a removed portion 118 of the first body panel web 110, a removed portion 128 of the second body panel web 120, and removed portions 156 of the absorbent composite 50. Removal of the various portions can be accomplished by known techniques, such as via cutter unit 158.

The method in particular embodiments can further comprise providing a supply 190 of absorbent composites 50. The method can further comprise attaching absorbent composites 50 to the leg elastic covering web 150 in a spaced apart manner (such as at cut-and-rotate attachment station 191). In such an embodiment, the series of absorbent composites 50, the leg elastic covering web 150, the front and back body panel webs 110, 120, the leg elastic members 140, 142, and the optional waistband webs 170, 180 together define the composite garment web 160. The method further includes folding the composite garment web 160 along a centerline 104 that extends in the machine direction 102 (such as at folding station 164), such that the first body panel web waist edge 111 is brought into close proximity with the second body panel web waist edge 121, and/or such that the first waistband web distal edge 174 is brought into close proximity with the second waistband web distal edge 184. The method in particular embodiments further includes attaching the first body panel web 110 to the second body panel web 120 along a series of garment side seam bonds 66 spaced apart in the machine direction 102. The method further includes cutting the composite garment web 160 at a series of cut locations spaced apart in the machine direction 102 to create the plurality of pant-like disposable absorbent garments 20. The seaming and cutting operations can occur at separate stations, or can occur at a single seaming and cutting station 166, as representatively illustrated in FIG. 1.

The present invention relates in another aspect to a pant-like disposable absorbent garment. Referring to FIGS. 4-7, the garment 20 defines a longitudinal direction 22 and a lateral direction 23 perpendicular to the longitudinal direction 22. As used in describing the various embodiments of the garment aspect of the present invention, the terms "longitudinal" and "lateral" have their customary meaning, as indicated by the longitudinal axis 24 and the lateral axis 25 depicted in FIGS. 5-7. The longitudinal axis 24 lies in the plane of the article when the article is in a fully stretched and laid-flat condition, prior to the joining of the front and back panels, and is generally parallel to a vertical plane that bisects a standing wearer into left and right body halves when the article is worn. The lateral axis 25 lies in the plane of the article and is generally perpendicular to the longitudinal axis 24. The garment 20 has a front region 30 defining a front waist end edge 32, a back region 34 defining a back waist end edge 36, and a crotch region 38 positioned longitudinally between the front region 30 and the back region 34. The crotch region 38 defines two laterally opposed crotch side edges 39. The garment 20 defines a garment length 21 that extends from the front waist end edge 32 to the back waist end edge 36.

The garment 20 includes an elastomeric film laminate front panel 40 which defines a front panel waist edge 42, a front panel leg edge 44 spaced longitudinally inward from the front panel waist edge 42, and first and second laterally opposed front panel side edges 46, 48 which extend longitudinally between the front panel waist edge 42 and the front panel leg edge 44. The garment 20 also includes an elastomeric film laminate back panel 41 which defines a back panel waist edge 43, a back panel leg edge 45 spaced longitudinally inward from the back panel waist edge 43, and first and second laterally opposed back panel side edges 47, 49 which extend longitudinally between the back panel waist edge 43 and the back panel leg edge 45. "Longitudinally inward" as used to describe garment embodiments herein means in a direction longitudinally toward the central lateral axis 25. The front panel 40 is longitudinally spaced apart from the back panel 41. Examples of suitable elastomeric film laminates are discussed above in conjunction with the method aspect of the invention. In preferred embodiments, both the elastomeric film laminate front panel 40 and the elastomeric film laminate back panel 41 comprise an elastomeric film layer sandwiched between two nonwoven facing layers, as representatively illustrated in FIG. 1a in conjunction with the method aspect of the present invention.

The garment further includes at least one front leg elastic member 70 disposed adjacent the front panel leg edge 44, and at least one back leg elastic member 75 disposed adjacent the back panel leg edge 45. Examples of suitable leg elastic materials are discussed above in conjunction with the method aspect of the invention. In particular embodiments, the back leg elastic member 75 and/or the front leg elastic member 70 extends laterally across the entire garment width. In other embodiments, such as that representatively illustrated in FIGS. 4 and 5, the back leg elastic member 75 can comprise a pair of back leg elastic members, such as first and second back leg elastic members 76, 77 positioned on opposite sides of the absorbent composite 50. Similarly, the front leg elastic member 70 can comprise a pair of front leg elastic members, such as first and second front leg elastic members 71, 72 positioned on opposite sides of the absorbent composite 50. In preferred embodiments, such as that representatively illustrated in FIGS. 4 and 5, each back leg elastic member 75 can comprise a plurality of elastomeric threads, and/or each front leg elastic member 70 can comprise a plurality of elastomeric threads.

The garment also includes a leg elastic covering panel 60 which extends between and interconnects the front panel 40 to the back panel 41. Preferably (but optionally), the covering panel 60 is comprised of a non-elastomeric nonwoven material, such as a spunbond, a spunbond laminate, a bonded-carded web, or the like, examples of which are known in the art. The front leg elastic member 70 is sandwiched between the leg elastic covering panel 60 and the front panel 40, and the back leg elastic member 75 is sandwiched between the leg elastic covering panel 60 and the back panel 41. The leg elastic covering panel defines a length 61 extending in the longitudinal direction 22. In particular embodiments, the length 61 of the leg elastic covering panel 60 is less than the garment length 21. For example, in particular embodiment the length 61 of the leg elastic covering panel 60 is at most 80 percent, more particularly at most 70 percent, and still more particularly at most 60 percent of the garment length 21. Making the leg elastic covering panel length 61 relatively shorter than the garment length 21 as just described can improve manufacturing ease and reduce cost, while still providing the desirable function of covering and securing the leg elastic members 70/75. In another example, the leg elastic covering panel 60 defines a laterally extending covering panel front region edge 62 and a laterally extending covering panel back region edge 63. The covering panel front region edge 62 is positioned longitudinally inward of the front panel waist edge 42, and the covering panel back region edge 63 is positioned longitudinally inward of the back panel waist edge 43, such as by at least 2 centimeters, or more particularly by at least 5 centimeters.

In particular embodiments, an absorbent composite 50 is attached to the leg elastic covering panel 60. The absorbent composite 50 comprises a liquid impermeable barrier layer 52 defining a width 53, an absorbent core 54 comprised of liquid-absorbing materials such as cellulosic fluff and/or superabsorbent polymer, a liquid permeable liner 55, and crotch elastic members 56. The leg elastic covering panel 60 defines a maximum front width 64 and a maximum back width 65. In particular embodiments, the maximum front width 64 and the maximum back width 65 of the leg elastic covering panel 60 both exceed the barrier layer width 53. For example, in one embodiment, the maximum front width 64 and the maximum back width 65 of the leg elastic covering panel 60 are both at least twice that of the barrier layer width 53. In one embodiment, the length 51 of the absorbent composite 50 is at least 10 percent greater than the leg elastic covering panel length 61. In addition or in the alternative, the front width 64 and/or the back width 65 of the leg elastic covering panel 60 are/is at least 50 percent greater, or more particularly at least 100 percent greater, than the liquid impermeable layer width 53. In certain embodiments, such as that representatively illustrated in FIG. 5, the leg elastic covering panel defines a generally hourglass shape.

In particular embodiments, the front region 30 further comprises a front elastomeric waistband 80 attached to the front panel 40 adjacent the front panel waist edge 42, and/or the back region 34 comprises a back elastomeric waistband 81 attached to the back panel 41 adjacent the back panel waist edge 43. A pair of side seams 84, 84 connects the front region 30 to the back region 34, such that the garment 20 defines a waist opening 27 and a pair of leg openings 28. The side seams can be permanent but tearable, such as by way of adhesive, thermal, or ultrasonic bonding, or can be more readily releasable as well as refastenable, such as via the use of mechanical fastening elements.

It will be appreciated that details of the foregoing embodiments, given for purposes of illustration, are not to be construed as limiting the scope of this invention. Although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A pant-like disposable absorbent garment defining a longitudinal direction and a lateral direction perpendicular to the longitudinal direction, the garment having a front region defining a front waist end edge, a back region defining a back waist end edge, and a crotch region longitudinally between the front and back regions, the crotch region defining two laterally opposed crotch side edges, and the garment defining a garment length extending from the front waist end edge to the back waist end edge, the garment comprising:

an elastomeric film laminate front panel which defines a front panel waist edge, a front panel leg edge spaced longitudinally inward from the front panel waist edge, and first and second laterally opposed front panel side edges which extend longitudinally between the front panel waist edge and the front panel leg edge;

an elastomeric film laminate back panel which defines a back panel waist edge, a back panel leg edge spaced longitudinally inward from the back panel waist edge, and first and second laterally opposed back panel side edges which extend longitudinally between the back panel waist edge and the back panel leg edge, wherein the front panel is longitudinally spaced apart from the back panel;

at least one front leg elastic member disposed adjacent the front panel leg edge, and at least one back leg elastic member disposed adjacent the back panel leg edge;

a leg elastic covering panel which extends between and interconnects the front panel to the back panel such that the front leg elastic member is sandwiched between the leg elastic covering panel and the front panel and such that the back leg elastic member is sandwiched between the leg elastic covering panel and the back panel;

wherein a length of the leg elastic covering panel is less than the garment length;

an absorbent composite attached to the leg elastic covering panel; and a pair of side seams connecting the front region to the back region, thereby defining a waist opening and a pair of leg openings.

2. The garment of claim 1 wherein both the elastomeric film laminate front panel and the elastomeric film laminate back panel each comprise an elastomeric film layer sandwiched between two nonwoven facing layers.

3. The garment of claim 1 further comprising a pair of back leg elastic members positioned on opposite sides of the absorbent composite.

4. The garment of claim 3 wherein each back leg elastic member comprises a plurality of elastomeric threads.

5. The garment of claim 3 further comprising a pair of front leg elastic members positioned on opposite sides of the absorbent composite.

6. The garment of claim 1 wherein the front region comprises a front elastomeric waistband attached to the front panel adjacent the front panel waist edge, and wherein the back region comprises a back elastomeric waistband attached to the back panel adjacent the back panel waist edge.

7. The garment of claim 1 wherein the absorbent composite comprises a liquid impermeable barrier layer defining a width, and wherein the leg elastic covering layer defines a maximum front width and a maximum back width, and wherein the maximum front width and the maximum back width of the leg elastic covering layer both exceed the barrier layer width.

8. The garment of claim 1 wherein the leg elastic covering panel defines a covering panel front region edge and a covering panel back region edge, and wherein the covering panel front region edge is positioned longitudinally inward of the front panel waist edge and wherein the covering panel back region edge is positioned longitudinally inward of the back panel waist edge.

* * * * *